United States Patent [19]

Dumont et al.

[11] 3,993,764
[45] Nov. 23, 1976

[54] TREATMENT OF DEPRESSIVE STATES AND PARKINSON'S DISEASE

[75] Inventors: Claude Dumont, Nogent-sur-Marne; Jacques Laurent, Chilly-Mazarin, both of France

[73] Assignee: Roussel-UCLAF, Paris, France

[22] Filed: Nov. 28, 1975

[21] Appl. No.: 636,098

[30] Foreign Application Priority Data
Dec. 9, 1974 France .............................. 74.40233
Oct. 23, 1975 France .............................. 75.32483

[52] U.S. Cl. .............................................. 424/267
[51] Int. Cl.² ..................................... A61K 31/445
[58] Field of Search ................................ 424/267

[56] References Cited
OTHER PUBLICATIONS
Chem. Abst. (1) — vol. 80, (1974) — 120790f.
Chem. Abst. (2) — vol. 74 (197) — 22665a.

*Primary Examiner*—Stanley J. Friedman
*Attorney, Agent, or Firm*—Hammond & Littell

[57] ABSTRACT

Novel compositions having antidepressive, antiemetic and anti-Parkinson activities comprising an effective amount of at least one compound selected from the group consisting of 3-(4'-piperidyl)-indoles of the formula

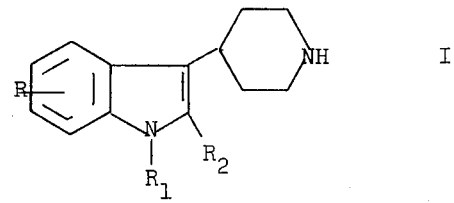

wherein R is selected from the group consisting of hydrogen and alkoxy of 1 to 5 carbon atoms and $R_1$ and $R_2$ are individually selected from the group consisting of hydrogen and alkyl of 1 to 5 carbon atoms and their non-toxic, pharmaceutically acceptable acid addition salts and a pharmaceutical carrier and to a method of treating depressive states and Parkinson disease in warm-blooded animals and humans.

8 Claims, No Drawings

TREATMENT OF DEPRESSIVE STATES AND PARKINSON'S DISEASE

OBJECTS OF THE INVENTION

It is an object of the invention to provide novel compositions having antiemetic, antidepressive and anti-Parkinson disease activity.

It is another object of the invention to provide a novel method of treating depressive states and Parkinson disease in warm-blooded animals and humans.

It is a further object of the invention to provide the non-toxic, pharmaceutically acceptable acid addition salts of the indoles of formula I.

These and other objects and advantages of the invention will become obvious from the following detailed description.

THE INVENTION

The novel compositions of the invention having antidepressive, antiemetic and anti-Parkinson disease activity are comprised of an effective amount of at least one compound selected from the group consisting of 3-(4'-piperidyl)-indoles of the formula

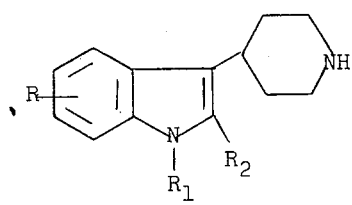

I wherein R is selected from the group consisting of hydrogen and alkoxy of 1 to 5 carbon atoms and $R_1$ and $R_2$ are individually selected from the group consisting of hydrogen and alkyl of 1 to 5 carbon atoms and their non-toxic, pharmaceutically acceptable acid addition salts and a pharmaceutical carrier.

In the compounds of formula I, R may be hydrogen or alkoxy of up to 5 carbon atoms such as methoxy, ethoxy or propoxy and $R_1$ and $R_2$ are hydrogen or alkyl of up to 5 carbon atoms such as methyl, ethyl, propyl, isopropyl or butyl. R is preferably hydrogen or methoxy and $R_1$ and $R_2$ are preferably hydrogen or methyl.

Examples of suitable acids for the formation of the acid addition salts of the indoles of formula I are inorganic acids such as hydrochloric acid, hydrobromic acid, hydroiodic acid, nitric acid, sulfuric acid or phosphoric acid and organic acids such as acetic acid, formic acid, benzoic acid, maleic acid, fumaric acid, succinic acid, tartaric acid, citric acid, oxalic acid, glyoxylic acid, aspartic acid, alkanesulfonic acids, arylsulfonic acids. Hydrochloric acid is preferred.

Examples of suitable compounds of formula I are 3-(4'-piperidyl)-indole, 1-methyl-3-(4'-piperidyl)-indole, 6-methoxy-3-(4'-piperidyl)-indole, 5-methoxy-3-(4'-piperidyl)-indole, 6-methoxy-2-methyl-3-(4'-piperidyl)-indole and their non-toxic, pharmaceutically acceptable acid addition salts, particularly the hydrochlorides.

The compositions of the invention are useful for the treatment of psychic troubles, behavior problems, character troubles as well as for the treatment of Parkinson disease and akinesia. The usual oral dose is 5 to 500 mg per day in humans.

The compositions may be in the form of simple tablets, dragees, gelules, granules, suppositories and injectable solutions or suspensions prepared in the usual manner.

The compositions will also contain the usual excipients such as talc, gum arabic, lactose, starch, magnesium stearate, cacao butter, aqueous or non-aqueous vehicles, animal or vegetable fatty bodies, paraffinic derivatives, glycols, preservatives and diverse wetting agents, dispersants or emulsifiers.

Some of the piperidyl-indoles of formula I are described in the literature and others are prepared by the process of Belgium Pat. No. 802,912. The acid addition salts are prepared in the usual fashion by reacting the free base with an approximately stoichiometric amount of the desired acid.

The novel method of the invention for the treatment of depressive states and Parkinson disease in warm-blooded animals or humans comprises administering to humans or warm-blooded animals an effective amount of at least one compound of formula I or their non-toxic, pharmaceutically acceptable acid addition salts. The compounds may be administered orally, rectally or parenterally. The usual daily dose is 0.3 to 1.5 mg/kg depending upon the specific product and the method of administration.

In the following examples there are described several preferred embodiments to illustrate the invention. However, it is to be understood that the invention is not intended to be limited to the specific embodiments.

EXAMPLE 1

3-(4'-piperidyl)-indole hydrochloride (compound A)

A suspension of 12 g of 3-(4'-piperidyl)-indole (prepared by the process of Belgium Pat. No. 802,912) in 70 ml of methanol was cooled in an ice-water bath and a methanol solution saturated with hydrochloric acid was slowly added thereto until a pH of 1 was reached (about 20 ml). The mixture was allowed to crystallize at 0° C for 30 minutes and was then filtered. The crystals were rinsed with methanol and dried under reduced pressure to obtain 12.5 g of raw hydrochloride salt. The crystals were dissolved in 160 ml of refluxing methanol and the solution was concentrated to about 100 ml. The mixture was allowed to crystallize for 3 hours at room temperature and 1 hour at 0° C and was then filtered. The crystals were rinsed with methanol and dried under reduced pressure to obtain 8.4 g of 3-(4'-piperidyl)-indole hydrochloride in the form of a cream product melting at 228° C.

| Analysis: | $C_{13}H_{17}ClN_2$ | | | |
|---|---|---|---|---|
| Calculated: | % C 65.95 | % H 7.24 | % N 11.83 | % Cl 14.98 |
| Found: | 65.9 | 7.3 | 11.7 | 15.0 |

EXAMPLE 2

1-methyl-3-(4'-piperidyl)-indole hydrochloride (compound C)

A solution of 26 g of 1-methyl-3-(4'-piperidyl)-indole in 210 ml of ethyl acetate was iced and then 30 ml of ethyl acetate saturated with hydrochloric acid were added thereto with stirring. The mixture was allowed to crystallize in the ice bath and was then filtered. The crystals were rinsed with ethyl acetate to obtain 19.2 g of product which was crystallized from refluxing ethanol to obtain 12 g of 1-methyl-3-(4'-piperidyl)-indole hydrochloride in the form of colorless crystals melting at 264° C.

| Analysis: | $C_{14}H_{19}ClN_2$ | | | |
|---|---|---|---|---|
| Calculated: | % C 67.05 | % H 7.63 | % Cl 14.14 | % N 11.17 |
| Found: | 66.9 | 7.4 | 14.2 | 11.1 |

EXAMPLE 3

5-methoxy-3-(4'-piperidyl)-indole hydrochloride (compound D)

A solution of 10 g of 5-methoxy-3-(4'-piperidyl)-indole in 100 ml of methanol was iced and 30 ml of ethyl acetate saturated with hydrochloric acid were added thereto followed by the addition of 100 ml of ethyl acetate. The mixture crystallized in the ice bath and was then filtered. The crystals were rinsed with ethyl acetate to obtain 11 g of product which was crystallized from refluxing ethanol to obtain 7.5 g of 5-methoxy-3-(4'-piperidyl)-indole hydrochloride in the form of colorless crystals melting at 217° C.

| Analysis: | $C_{14}H_{19}ClN_2O$ | | | |
|---|---|---|---|---|
| Calculated: | % C 63.03 | % H 7.18 | % N 10.50 | % Cl 13.29 |
| Found: | 62.9 | 7.1 | 10.3 | 13.1 |

EXAMPLE 4

6-methoxy-2-methyl-3-(4'-piperidyl)-indole hydrochloride (compound E)

A solution of 12.3 g of 6-methoxy-2-methyl-3-(4'-piperidyl)-indole (compound B) in 200 ml of ethanol was iced and an ethanolic solution of hydrochloric acid was added thereto with stirring at a temperature of less than 10° C until a pH of 1 was reached. The mixture was concentrated under reduced pressure and was then crystallized in a refrigerator and filtered. The crystals were washed with ethanol and dried under reduced pressure to obtain 12 g of product which was crystallized from refluxing ethanol to obtain 7.2 g of 6-methoxy-2-methyl-3-(4'-piperidyl)-indole hydrochloride in the form of beige crystals melting at 252° C.

| Analysis: | $C_{15}H_{21}ClN_2O$ | | | |
|---|---|---|---|---|
| Calculated: | % C 64.16 | % H 7.54 | % N 9.98 | % Cl 12.63 |
| Found: | 64.0 | 7.4 | 9.9 | 12.5 |

EXAMPLE 5

6-methoxy-3-(4'-piperidyl)-indole hydrochloride

A solution of 9.7 g of 6-methoxy-3-(4'-piperidyl)-indole in 60 ml of hot isopropanol was admixed with 15 ml of isopropanol saturated with hydrochloric acid and the crystals formed were redissolved by heating. The mixture was then filtered and the filtrate was concentrated and iced. The mixture was vacuum filtered and the crystals were rinsed with isopropanol and dried under reduced pressure to obtain 9.55 g of 6-methoxy-3-(4'-piperidyl)-indole hydrochloride in the form of colorless crystals melting at 213° C.

| Analysis: | $C_{14}H_{19}ClN_2O$ | | | |
|---|---|---|---|---|
| Calculated: | % C 63.03 | % H 7.18 | % N 10.5 | % Cl 13.29 |
| Found: | 63.1 | 7.3 | 10.3 | 13.5 |

EXAMPLE 6

Tablets were prepared containing 25 mg of 3-(4'-piperidyl)-indole hydrochloride or 1-methyl-3-(4'-piperidyl)-indole hydrochloride or 6-methoxy-2-methyl-3-(4'-piperidyl)-indole or its hydrochloride and sufficient excipient of lactose, starch, talc and magnesium stearate to obtain a tablet of 200 mg.

Injectable solutions were prepared containing 25 mg of 3-(4'-piperidyl)-indole hydrochloride or 5-methoxy-3-(4'-piperidyl)-indole hydrochloride and sufficient sterile water to obtain a volume of 2 ml.

PHARMACOLOGICAL DATA

A. Potentialization of stereotypes of amphetamine

The test was effected with groups of 5 male rats weighing between 150 and 180 g and each animal was individually placed in a grilled cage (29 × 25 × 17 cm) containing some scraps of wood chips and there was a delay of 1 hour between the administration of the test compound and the injection of 5 mg/kg of dexamphetamine sulfate. The behavior of the animals was noted every half hour for 5 hours with the reading as recommended by Halliwell et al [Brit. J. Pharmacol., Vol. 23 (1964), p. 330–350].

The animals were asleep (0), awake but immobile (1), turning in the cage (2), sniffing the cover (3), licking the sides (4), touching the wood chips or bars (5) or gnawing the wood chips or bars (6). The intensity of the stereotype is expressed in the form of a score of 0 to 30 corresponding to the values obtained from the 5 rats in each lot each time. The sum of the scores obtained in 5 hours was calculated. The test compounds were intraperitoneally administered in aqueous suspension (6-methoxy 2-methyl 3-(4'-piperidyl) indole, called compound B) or solution and the dose increasing by about 100% the total of the score in 5 hours was determined. The said doses were 20 mg/kg for compound A, 5 mg/kg for compound B, greater than 20 mg/kg for compound C, equal to about 1 mg/kg for compound D and about 5 mg/kg for compound E.

B. Antagonism against catalepsy of prochlorpemazine

The test used groups of 5 male rats weighing about 100 g and the test products were administered intraperitoneally or orally in aqueous solution simultaneously with an intraperitoneal dose of 15 mg/kg of prochlorpemazine. The catalepsy was determined every hour for 7 hours according to the test of crossing of homolateral paws by Boisser et al [Therapie, Vol. 18 (1963), p. 1257–77]. The ratings were as follows: the animals refused to cross the front paws with the same side rear paws (0), accepted the research crossing only on one side (0.5) or accepted the crossing on both sides (1). Compound A, opposed the catalepsy induced by prochlorpemazine at 0.5 mg/kg when administered intraperitoneally and at 2 mg/kg when orally administered. Compound C was effective at 10 mg/kg when administered intraperitoneally and compound D was effective at 2 mg/kg when administered intraperitoneally.

C. Antiemetic Activity

The antagonism against vomitting provoked by apomorphine was studied on dogs with the test of Chen et al [J. Pharmac. Exp. Therap., Vol. 93 (1959), p. 245–250]. The number of vomits provoked by a subcutaneous injection of 0.1 mg/kg of apomorphine hydrochloride was determined for each dog 8 days before the test. Compound A in aqueous solution was administered subcutaneously in variable doses ½ hour before the apomorphine hydrochloride and the antagonist dose to vomitting was 0.5 mg/kg for compound A.

D. Acute Toxicity

The acute toxicity was determined on groups of 10 mice weighing about 20 g which received orally or intraperitoneally increasing doses of compounds A, C, D and E and the mortality was determined 48 hours after the administration of the test compound. The $DL_{50}$ dose which killed 50% of the animals for compound A was 95 mg/kg intraperitoneally and 200 mg/kg orally. The $DL_{50}$ doses for C, D and E were 60 mg/kg, 100 mg/kg and 95 mg/kg, respectively, when administered intraperitoneally.

Various modifications of the compositions and method of the invention may be made without departing from the spirit or scope thereof and it is to be understood that the invention is intended to be limited only as defined in the appended claims.

We claim:

1. A method of treating depressive states and symptoms of Parkinson disease in humans comprising administering to humans an effective amount of at least one compound selected from the group consisting of 3-(4'-piperidyl)-indoles of the formula

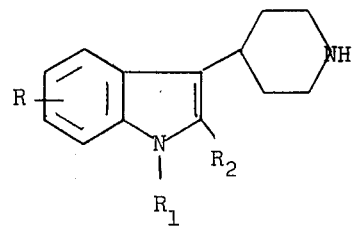

wherein R is selected from the group consisting of hydrogen and alkoxy of 1 to 5 carbon atoms and $R_1$ and $R_2$ are individually selected from the group consisting of hydrogen and alkyl of 1 to 5 carbon atoms and their non-toxic, pharmaceutically acceptable acid addition salts.

2. The method of claim 1 wherein the compound is in the form of its non-toxic, pharmaceutically acceptable acid addition salt.

3. The method of claim 2 wherein the compound is 3-(4'-piperidyl)-indole hydrochloride.

4. A method according to claim 1 wherein the compound is a salt of 3-(4'-piperidyl)-indole.

5. A method according to claim 1 wherein the compound is a salt of 1-methyl-3-(4'-piperidyl)-indole.

6. A method according to claim 1 wherein the compound is a salt of 5-methoxy-3-(4'-piperidyl)-indole.

7. A method according to claim 1 wherein the compound is a salt of 6-methoxy-3-(4'-piperidyl)-indole.

8. A method according to claim 1 wherein the compound is a salt of 6-methoxy-2-methyl-3-(4'-piperidyl)-indole.

* * * * *